United States Patent [19]

Auriol et al.

[11] Patent Number: 4,956,489
[45] Date of Patent: Sep. 11, 1990

[54] WATER-SOLUBLE L-TYROSINE DERIVATIVES AND A PROCESS FOR PREPARING L-TYROSINE DERIVATIVES

[75] Inventors: Daniel H. Auriol; Francois B. Paul, both of Toulouse; Pierre F. Monsan, Blagnac, all of France

[73] Assignee: Bioeurope, France

[21] Appl. No.: 257,823

[22] Filed: Oct. 14, 1988

[30] Foreign Application Priority Data

Oct. 19, 1987 [FR] France ................ 87 14352

[51] Int. Cl.$^5$ .................................... C07C 101/32
[52] U.S. Cl. .................... 560/40; 562/445; 564/165
[58] Field of Search ............ 562/445; 564/165; 560/40

[56] References Cited

FOREIGN PATENT DOCUMENTS 2608174 7/1977 Fed. Rep. of Germany .
2917603 11/1980 Fed. Rep. of Germany ...... 562/445

OTHER PUBLICATIONS

Bachmayer et al, Biochim. Biophys. Acta, vol. 302, pp. 399–405 (1973).
Journal of Medicinal Chemistry, vol. 29, No. 6, Jun. 1986, pp. 906–912, The American Chemical Society; Y. Miyashita, French Search Report.

Primary Examiner—Bruce Gray
Attorney, Agent, or Firm—Stevens, Davis, Miller & Mosher

[57] ABSTRACT

The invention relates to the preparation of water-soluble L-tyrosine derivatives having the formula

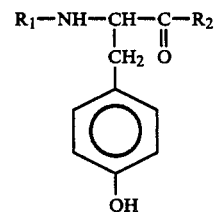

where $R_1$ is a L-malyl, L-lactyl, L-glutamyl or L-aspartyl group, $R_2$ is a —OH, —OM, methoxy, ethoxy or amino group and M is an alkaline metal, by enzymatic condensation of an acid selected among L-malic, L-lactic, L-glutamic and L-aspartic acids, with a L-tyrosine derivatives selected among the ethyl and methyl esters and the amide of L-tyrosine. The enzyme is obtained from a culture of *Micrococcus casealyticus*. The compounds where $R_1$ is a L-malyl or L-lactyl group are new. Said L-tyrosine derivatives are useful in cosmetic and pharmaceutical compositions, such as tanning and sun compositions.

2 Claims, No Drawings

WATER-SOLUBLE L-TYROSINE DERIVATIVES AND A PROCESS FOR PREPARING L-TYROSINE DERIVATIVES

The invention relates to new water-soluble L-tyrosine derivatives, and to a process for preparing L-tyrosine derivatives.

L-Tyrosine is an important amino acid for human beings. One of the biosynthetic pathways of utilization of L-tyrosine is that leading to the formation of melanin in human skin.

The use of L-tyrosine in cosmetic products dates back some 15 years in the U.S.A. The object of these first uses was to stimulate melanin biosynthesis, and hence the natural pigmentation of white skin, by an external provision of amino acid. By this means, a self-generated protection against the sun could be expected.

At the present time, sun products that stimulate melanogenesis turn this property of L-tyrosine to good account. Nevertheless, L-tyrosine has the drawback of being only slightly soluble in all solvents, even in the form of a salt with sodium, potassium, amines or strong bases, at pH values in the region of neutrality. This obviously limits its use.

It would hence be useful to have water-soluble L-tyrosine derivatives, capable both of crossing the cutaneous barrier and of being converted in the skin to metabolizable L-tyrosine. This objective can be achieved by means of the present invention.

More especially, the invention relates to new L-tyrosine derivatives, characterized in that they have the general formula

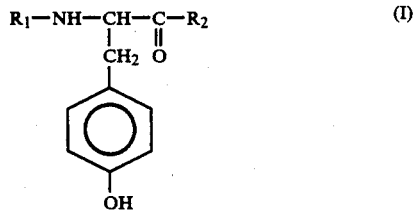

(I)

where $R_1$ is an L-malyl or L-lactyl group and $R_2$ is an —OH, —OM, methoxy, ethoxy or amino group, M denoting an alkali metal.

To date, the derivatives of the general formula I in which $R_2$ is an —OH or —OM group, M being an alkali metal, especially Na or K, are preferred.

The invention also relates to a process for preparing an L-tyrosine derivative having the general formula I above, where $R_1$ is an L-malyl, L-lactyl, L-glutamyl or L-aspartyl group and $R_2$ is an —OH, —OM, methoxy, ethoxy or amino group, M denoting an alkali metal, characterized in that an acid chosen from L-malic, L-lactic, L-glutamic and L-aspartic acids and their salts is condensed enzymatically, in an aqueous medium, with a starting L-tyrosine derivative chosen from the ethyl and methyl esters and the amide of L-tyrosine, in the presence of a multimeric enzyme possessing a molar mass greater than 100,000, not exhibiting any proteolytic activity with respect to casein and either extracted (extracellular enzyme) from the culture broth of Micrococcus caseolyticus remaining after separation of the Micrococcus caseolyticus cells, or extracted (intracellular enzyme) from Micrococcus caseolyticus cells, or alternatively in the presence of Micrococcus caseolyticus cells.

It should be noted that the terms "L-malyl, L-lactyl, L-glutamyl and L-aspartyl groups" encompass both the L-malyl, L-lactyl, L-glutamyl and L-aspartyl groups themselves, and their salts, especially with alkali metals such as Na or K.

According to an especially preferred embodiment, the aqueous medium contains a cosolvent chosen from the compounds of general formula II:

(II)

in which R is a methyl group and n is an integer from 1 to 50, and preferably from 1 to 15, glycerol, polyols (such as butanediols and propanediol), ethylene glycol, polyethylene glycols of formula

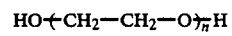

where n=2-800, and preferably 2-50, N,N-dimethylacetamide (DMA), 1,3-dimethyl-2-imidazolidinone (DMI) and tetrahydrothiophene 1,1-dioxide (known as "Sulfolane").

Preferably, the reaction medium contains, in addition, manganese or zinc cations (these latter exclusively when the cosolvent corresponds to the formula (II) to accelerate the reaction.

The starting acid may be used in the form of the free acid or of one of its salts, for example the sodium or potassium salt. The use of a salt of the acid has the advantage of simplifying the adjustment of the pH of the reaction medium. Since the condensation reaction is stereospecific, the starting acid can be in the stereospecifically pure L form or the form of the DL racemic mixture. In this latter case, only the L form will be consumed by the reaction, the D form not being "recognized" by the enzyme.

The starting L-tyrosine derivative may be used as such or in the form of an addition salt with an acid, for example the hydrochloride, if desired. Racemic mixtures of L-tyrosine derivatives and D-tyrosine derivatives may also be used, if so desired, but only the L-tyrosine derivative will take part in the reaction, the enzyme having a stereospecific action, as in the case of the starting acid.

A molar proportion of the starting L-tyrosine derivative which is substantially equal to that of the starting acid, or greater than the proportion of the latter, will normally be used. The concentration of the starting L-tyrosine derivative can range, for example, from 50 to 500 mM, and preferably from 200 to 400 mM. That of the starting acid can range, for example, from 50 to 300 mM, and preferably from 100 to 200 mM.

The condensation reaction can be performed at a pH of 5 to 8, and preferably 6 to 7, and at a temperature of 10° to 50° C., and preferably approximately 30° to 45° C.

The condensation reaction can be performed in the presence of an enzyme described in French Patent No. 2,589,479 under the name of enzyme E. This patent also teaches a process for the preparation of this enzyme from the culture broth of Micrococcus caseolyticus (strain deposited at the Institut Pasteur in Paris under No. 1194) remaining after separation of the cells. It is also possible to use the modified enzyme version whose preparation is described in French Patent Application No. 2,609,376, filed on 14th January 1987.

Preferably, however, the intracellular enzyme present in Micrococcus caseolyticus cells, or even Micrococcus caseolyticus cells, is/are preferably used, since the Applicant has, in effect, realized that the active enzyme described in the abovementioned French patents was an intracellular enzyme present in the Micrococcus caseolyticus (strain No. 1194, deposited at the Institut Pasteur) cells, whose presence in the culture broth from which it is extracted in the processes of the abovementioned French patents was, as it were, accidental, resulting from the treatment applied to the culture in order to separate the Micrococcus caseolyticus cells from the broth, which causes the rupture of a small number of cells and hence the release of intracellular enzyme into the broth.

The intracellular enzyme may be prepared from a Micrococcus caseolyticus culture by separation of the Micrococcus caseolyticus cells, suspension of the latter in a suitable buffer, rupture of the cells by mechanical, ultrasonic, chemical or enzymatic means, centrifugation and collection of the supernatant, this being followed, if desired, by purification operations aimed at increasing the enzymatic activity and also removing certain enzymatic activities which may be detrimental to the reaction, such as an esterase activity which can lead to the removal of the group $R_2$ of the L-tyrosine derivative of general formula (I). In the same manner, this esterase activity can lead to the hydrolysis of the L-tyrosine ester or amide.

The Applicant has also found that it was also possible to use Micrococcus caseolyticus cells to carry out the condensation reaction.

In fact, the process of the invention may be carried out with preparations ranging from Micrococcus caseolyticus cells to highly purified preparations of intracellular enzyme.

The cosolvent, when used, will be present in the proportion of 20 to 75% (weight/volume), and preferably 50 to 60% (weight/volume), relative to the aqueous media (total water + cosolvent). Triglyme (2,5,8,11-tetraoxadodecane or triethylene glycol dimethyl ether) and polyethylene glycols are most especially preferred cosolvents, followed by diglyme (diethylene glycol dimethyl ether).

It has been found, in effect, that the presence of a high concentration of cosolvents increases the reaction yield, by shifting the equilibrium of the reaction towards the synthesis of the desired product. In addition, in the case of the use of Micrococcus caseolyticus cells, some cosolvents, such as the glymes of formula II, render the cell membranes permeable, thereby reinforcing the enzymatic activity of the cells.

Metal cations, such as zinc and/or manganese cations, if used, may be provided by compatible water-soluble salts, such as the chlorides or sulphates. Their concentration in the reaction medium in the form of water-soluble salts can range from 0.1 millimole to 5 millimoles per liter (equivalent to a molarity of 0.1 to 5 mM). Zinc ions are preferred, at a molarity of 0.5 to 5 mM. Manganese cations stabilize the enzyme, while zinc cations, which is used only when the cosolvent is a glyme of formula II, prevent the enzyme being inhibited by these glymes.

The order of addition of the various constituents is preferably such that the enzyme and the cosolvent, if one is used, are added after adjustment of the pH. It was observed, in effect, that the cosolvent could interfere with the pH measurement, which must be correctly adjusted before the enzyme is added.

Advantageously, the preparation of the reaction medium can be carried out in the following order:
 (a) dissolution of the starting L-tyrosine derivative and the acid in water and pH adjustment,
 (b) addition of the cosolvent,
 (c) optional addition of metal cations, and
 (d) addition of the enzyme; it being possible, however, for the stage (c) to be performed before the stage (b).

The reaction time can range from 1 to 36 hours, and preferably from 12 to 24 hours. It will vary according to the temperature, the concentration of enzyme used and the nature and concentration of any cosolvent. As a guide, enzyme concentrations ranging from 5 to 100 units/milliliter of reaction medium may be employed.

The L-tyrosine derivatives of the invention are characterized by a high solubility in water, of the order of several hundred grammes per liter, which makes them eminently useful for the formulation of compositions for cosmetic use (photosensitizing creams, for example) or pharmaceutical use (for parenteral feeding, for example).

The non-limiting examples which follow are given for the purpose of illustrating the invention.

In the examples, the L-tyrosine derivatives produced were analysed by an HPLC method (Millipore-Waters chromatograph) using a MicroBondapack C18 column (Millipore-Waters, length: 30 cm; diameter: 4.7 mm). The elution solvent had the following composition:
 acetonitrile: 9% (v/v)
 12.5 mM monosodium phosphate, pH 3.5: 91% (v/v).

The eluent flow rate was 2 ml/min and the column temperature was 40° C.

The detection of the compounds was carried out using a spectrophotometer whose wavelength was set at 254 nm. The concentration of the products was determined using the absorption coefficient of l-tyrosine:

($\epsilon 254$ nm = 0.36 mM$^{-1}$.cm$^{-1}$).

The enzyme used in Examples 1-6 had been produced according to the teachings of the above-mentioned French patent Application No. 2,609,316. This enzyme was in free form. It should be noted, however, that the enzyme could also be employed in immobilized form on an appropriate support.

EXAMPLE 1

Production and purification of L-malyl-L-tyrosine (disodium salt)

(1) Synthesis of L-malyl-L-tyrosine ethyl ester:

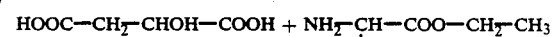

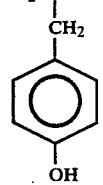

L-Malic acid + L-Tyrosine ethyl ester →

HOOC—CH₂—CHOH—CO—NH—CH—COO—CH₂—CH₃
                              |
                             CH₂
                              |
                           (C₆H₄)
                              |
                             OH

EXPERIMENT NO. 1

The reaction medium is prepared as follows:

Dissolution of 9.4 g of L-malic acid (molar mass 134) and 34.3 g of L-tyrosine ethyl ester hydrochloride in 60 g of demineralized water. The pH of the solution is adjusted to 0.4 using 4N sodium hydroxide, which converts the L-malic acid to sodium L-malate. 0.9 ml of a 0.2M zinc sulphate solution is added. The weight of this solution is adjusted to 151 g with demineralized water.

Addition of 192 g of triglyme (molar mass: 178.2). The reaction medium is stirred magnetically until a homogeneous solution is obtained, and placed in a thermostated incubator at 40° C.

The reaction is started by adding 7 g of the stock solution of enzyme. This stock solution has an activity equal to 1,000 U/g, measured under the following conditions:

L-malyl-L-tyrosine ethyl ester: 17 mM
pH 6.4
temperature: 40° C.

The reaction is followed by the liberation of L-tyrosine ethyl ester with the passage of time (HPLC analysis described above). The enzyme unit U corresponds to the hydrolysis of one micromole of L-malyl-L-tyrosine ethyl ester per hour.

In the resulting reaction medium, the concentrations of the ingredients were as follows: sodium malate: 200 mM; L-tyrosine ethyl ester: 400 mM; triglyme: 55% (weight/volume); zinc chloride: 0.5 mM; and enzyme: 20 U/ml.

The reaction medium is incubated with gentle agitation for 15 hours. When the enzymatic reaction is complete, the denaturation of the enzyme is produced by acidifying the reaction medium using 8 ml of 2N HCl until a pH of between 3 and 4 is obtained.

EXPERIMENTS NOS. 2 TO 4

The procedure was as in Experiment No. 1, except that the concentrations of the ingredients of the reaction medium were as summarized in Table 1 below, which also repeats the conditions used in Experiment No. 1.

TABLE 1

|  | Exp. 1 | Exp. 2 | Exp. 3 | Exp. 4 |
|---|---|---|---|---|
| Na L-malate, mM | 200 | 100 | 100 | 100 |
| L-Tyrosine ethyl ester, mM | 400 | 100 | 250 | 250 |
| Triglyme, % (w/v) | 55 | 55 | 55 | 0 |
| ZnCl₂, mM | 0.5 | 0.5 | 0.5 | 0 |
| Enzyme, U/ml | 20 | 20 | 20 | 20 |

After the reaction, the reaction media are analysed by the HPLC method described above. The results summarized in Table 2 below were obtained.

TABLE

| Final concentrations of L-malyl-L-tyrosine ethyl ester in the reaction media after 15 hours' incubation | | | | |
|---|---|---|---|---|
| Experiment | 1 | 2 | 3 | 4 |
| L-malyl-L-tyrosine ethyl ester, mM* | 149 | 61 | 91 | 19 |
| Yield**, % |  | 74 | 61 | 91 | 19 |

*The concentrations were determined by the HPLC method described above before the final acidification stage.
**Calculated on the basis of the initial molar concentration of the starting acid (2) Purification of L-malyl-L-tyrosine ethyl ester This purification was carried out on the medium obtained in Experiment No. 1. This medium, of volume 350 ml, contains 17 g of L-malyl-L-tyrosine ethyl ester.

The first step is to dilute the reaction medium with water so as to bring the total volume to 1 liter.

The first purification stage consists in forming several successive extractions with 1.5 liters of toluene, a solvent which is not miscible with water, so as to remove most of the triglyme. After two successive extractions, the volume of the final aqueous phase, which contains 16.2 g of L-malyl-L-tyrosine ethyl ester, is 855 ml. The yield is 95%.

The aqueous phase (855 ml) is then subjected to an extraction with 3 liters of ethyl acetate, a volatile solvent which is not miscible with water, so as to extract the L-malyl-L-tyrosine ethyl ester (with the acid group of the malyl fragment in the free acid form) into the ethyl acetate phase. The ethyl acetate is then removed by evaporation under vacuum at 40° C., so as to obtain 15.2 g of pure product (yield: 89%). The product is dissolved in water to a volume of 750 ml.

The product is then de-esterified so as to obtain the desired final product, L-malyl-L-tyrosine in the form of its disodium salt. This operation is carried out using an enzyme, chymotrypsin (E.C. 3.4.21.1.):

$$\text{L-malyl-L-tyrosine ethyl ester} + H_2O \xrightarrow{\alpha\text{-chymotrypsin}} \text{L-malyl-L-tyrosine} + \text{ethanol}$$

Conditions of the enzymatic de-esterification:
α-chymotrypsin (SIGMA Ref. C 4129): 30 U/ml
pH 7.5 maintained constant using 4N sodium hydroxide
temperature = 37° C.

After this operation, the chymotrypsin is removed by ultrafiltration (AMICON hollow-fibre module; cut-off threshold; 10,000 daltons). The ultrafiltrate, which contains the L-malyl-L-tyrosine, is concentrated by evaporation under vacuo. Final volume: 600 ml.

The amounts of residual solvent present in the final aqueous phase are removed by extraction with 2 liters of ethyl acetate. The de-esterified product in the form of the disodium salt is not soluble in ethyl acetate, and remains entirely in the aqueous phase. The aqueous phase is then concentrated by evaporation under vacuo, after which it is lyophilized. The structure of the product was verified by elemental analysis and proton NMR spectroscopy. The solubility of L-malyl-L-tyrosine disodium salt (molar mass: 341) in water at 25° C. and pH 6 is 820 g/l, equivalent to 2.40 mole/liter.

EXAMPLE 2

Synthesis of L-malyl-L-tyrosine methyl ester

Working conditions identical to those of Example 1, except as regards:
L-tyrosine methyl ester hydrochloride: 0.25M
sodium malate: 0.1M After 20 hours' incubation at 40° C., the concentration of L-malyl-L-tyrosine methyl ester is 86 mM, which corresponds to a yield equal to 86% (calculated on the basis of the initial concentration of L-malic acid). This value is substantially equal to the yield obtained with L-tyrosine ethyl ester.

The ester obtained may be purified and deesterified as described in Example 1.

L-Tyrosine esters are relatively unstable in aqueous solution (especially as regards the methyl ester); a spontaneous de-esterification is observed, leading to the formation of a precipitate as a result of the very low solubility of L-tyrosine in free form. Accordingly, the enzymatic condensation reaction must be sufficiently fast to avoid a significant degradation of the substrate.

EXAMPLE 3

Enzymatic synthesis of L-lactyl-L-tyrosine (monosodium salt)

(A) Synthesis of L-lactyl-L-tyrosine ethyl ester $$CH_3-CHOH-COOH + NH_2-CH(CH_2-C_6H_4-OH)-COO-CH_2-CH_3$$

L-Lactic acid        L-Tyrosineethyl ester $$\downarrow\uparrow$$

$$CH_3-CHOH-CO-NH-CH(CH_2-C_6H_4-OH)-COO-CH_2-CH_3$$

The conditions of synthesis are identical to those described in Examples 1 and 2, except as regards:
sodium L-lactate: 0.1M
L-tyrosine ethyl ester: 0.25M Two syntheses were performed, one in the presence of 55% of triglyme, the other in the absence of cosolvent. The data and results are summarized in Table 3.

TABLE 3

| | Enzymatic synthesis of L-lactyl-L-tyrosine ethyl ester Concentration of L-lactyl-L-tyrosine ethyl ester, mM | |
|---|---|---|
| Incubation time hours | Experiment 1 In the presence of 55% (w/v) of triglyme | Experiment 2 Without cosolvent |
| 5 | 40 | 6 |
| 20 | 64 | 13 |
| 28 | 66 | 16 |
| Final yield | 66 | 16 |

TABLE 3-continued

| | Enzymatic synthesis of L-lactyl-L-tyrosine ethyl ester Concentration of L-lactyl-L-tyrosine ethyl ester, mM | |
|---|---|---|
| Incubation time hours | Experiment 1 In the presence of 55% (w/v) of triglyme | Experiment 2 Without cosolvent |
| of the reaction | | |

(b) The lactyl-L-tyrosine ethyl ester is purified and deesterified according to the procedure described in Example 1 in relation to L-malyl-L-tyrosine ethyl ester, to obtain L-lactyl-L-tyrosine monosodium salt. This salt (molar mass: 274) has a solubility in water at 25° C. and pH 6 at least equal to 330 g/liter, equivalent to 1.2 mole/liter.

EXAMPLE 4

Demonstration of the stereospecificity of the synthesis with respect to the organic acid (L-malic acid and L-lactic acid)

(a) Test of synthesis with sodium D-malate

The procedure is as in Example 1, with the exception of the following experimental conditions:
Sodium D-malate: 0.1M
L-tyrosine ethyl ester: 0.25M
Incubation: 18 hours The sodium D-malate was prepared by neutralization of D-malic acid (SIGMA M 0750) using 4N sodium hydroxide. This product contains 2.5% of L isomer.

After 18 hours' incubation, a concentration of malyl-L-tyrosine ethyl ester equal to 2.2 mM is measured, which corresponds to the concentration of the L isomer in the starting substance. The D isomer of malic acid is hence not recognized by the enzyme.

(b) Synthesis of L-malyl-L-tyrosine ethyl ester in the presence of sodium DL-malate (racemic mixture)

The procedure is as in Example 1, with the exception of the following experimental conditions:
Sodium DL-malate: 0.1M
L-tyrosine ethyl ester: 0.25M
Incubation: 18 hours.

After 18 hours' incubation, a concentration of L-malyl-L-tyrosine ethyl ester equal to 37 mM is measured, which corresponds to a 75% yield (calculated on the basis of the initial concentration of malic acid in L form (50 mM)).

This result confirms the stereospecificity of the enzymatic reaction with respect to L-malic acid.

(c) Test of synthesis in the presence of sodium D-lactate

The procedure is as in Example 1, with the exception of the following experimental conditions:
Sodium D-lactate: 0.1M
L-tyrosine ethyl ester: 0.25M
Incubation: 21 hours After 21 hours' incubation, no synthesis is observed.

(d) Synthesis of L-lactyl-L-tyrosine ethyl ester in the presence of sodium DL-lactate The procedure is as in Example 1, with the exception of the following experimental conditions:
Sodium DL-lactate: 0.1M
L-tyrosine ethyl ester: 0.25M
Incubation: 16 hours After 16 hours' incubation, the synthesis of L-lactyl-L-tyrosine ethyl ester at a concentration equal to 38 mM is observed. This result confirms the stereospecificity of the reaction with respect to L-lactic acid.

EXAMPLE 5

Synthesis of L-malyl-L-tyrosinamide

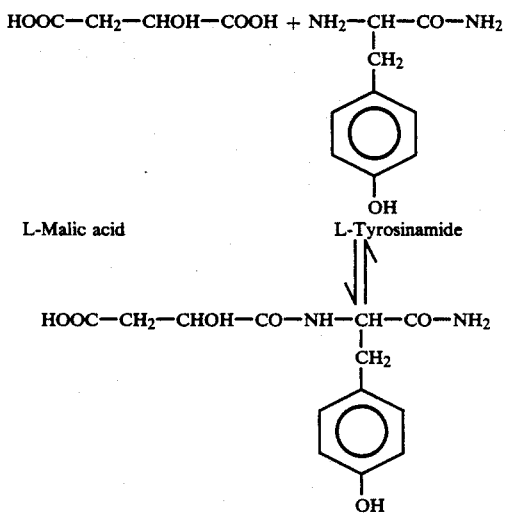

The procedure is as in Example 1, with the exception of the following experimental conditions:
Sodium L-malate: 0.1M
L-tyrosinamide: 0.25M
Incubation: 18 hours After 18 hours' incubation, a concentration of product equal to 85 mM is measured. The yield of this reaction is 85%. On repeating the synthesis in the absence of cosolvent (triglyme), a concentration of product equal to only 12 mM is measured. The product, L-malyl-L-tyrosinamide, may be readily deamidated with chymotrypsin as described in Example 1.

EXAMPLE 6

Synthesis of the ethyl esters of L-aspartyl-L-tyrosine and of L-glutamyl-L-tyrosine The reactions were performed according to the general procedure and the conditions of Example 1, except for the following conditions:
Temperature: 30° C.
Sodium L-aspartate or L-glutamate: 0.1M
L-tyrosine ethyl ester: 0.25M
Zinc sulphate: 1 mM
Enzyme concentration: 100 U/ml
Incubation: 18 hours The compounds of the title were obtained at respective concentrations of 6.6 and 17 mM, which corresponds to yields of 6.6 and 17%, respectively.

In the examples which follow, the purified intracellular enzyme extracted from Micrococcus caseolyticus cells was used as the enzyme. This enzyme was prepared by the following procedure:

Starting with Micrococcus caseolyticus strain No. 1194, deposited at the Institut Pasteur, a culture is made in the traditional manner, for example as described by M. DESMAZEAUD and J. HERMIER in the following publications:

Ann. Biol. Anim. Biochim. Biophys., 8, 419 (1968)
Ann. Biol. Anim. Biochim. Biophys., 8, 565 (1968)
Eur. J. Biochem., 19, 51–55 (1971).

The Micrococcus caseolyticus cells are harvested by centrifugation (8,000 g, 20 minutes, 4° C.) from the culture broth having a volume of 10 liters. The centrifugation pellet, consisting of the cells, is diluted in a 20 mM potassium phosphate buffer, pH 6.5, containing 0.1 mM manganese sulphate, to a volume of 1.5 liters.

The resulting cell suspension is subjected to the action of a homogenizer, for example consisting of a ball mill or a French press or a Manton-Gaulin apparatus, for the purpose of rupturing the cells. As a variant, the cells could also be ruptured by an enzymatic method, for example by the action of lysozyme. The rupturing of the cells is performed at 4° C. and until at least 90% of ruptured cells is obtained. After this, the ruptured cell suspension is diluted with a volume of the abovementioned potassium phosphate buffer equal to the volume added previously, and then centrifuged (8,000 g, 30 minutes, 4° C.). The solution obtained has an enzyme activity of 6.7 U/ml. The following purification operations are then performed:

The first step is to remove nucleic acids from the solution by adding to the solution 1.3 g of protamine sulphate per liter of solution, and then allowing reaction to take place for 2 hours at 4° C. so as to precipitate the nucleic acids, this being followed by centrifugation (8,000 g, 4° C., 1 hour) aimed at separating the precipitate from the remainder of the solution. The solution obtained contains all the enzyme activity. This solution is subjected to an ultrafiltration using a membrane possessing a cut-off threshold of 10,000 daltons. The retentate obtained contains all the enzyme activity. This retentate is subjected to ion exchange chromatography, for example on a column packed with DEAE-Sepharose ®, sold by PHARMACIA, by dissolving it in 20 mM potassium phosphate buffer, pH 6.5, containing 0.1 mM manganese sulphate, allowing the column packing to absorb the solution, and then eluting using KCl solutions of a molarity varying continuously from 0 to 1M. It is found that the enzyme is mainly eluted in the fraction corresponding to approximately 300 mM KCl.

The eluted fraction containing the enzyme is then desalted and concentrated by ultrafiltration using a membrane possessing a cut-off threshold of 10,000 daltons. The yield of this stage is of the order of approximately 70%. The enzyme preparation thereby obtained, which has an enzyme activity of 55 U/ml, is used in the examples which follow, but the purification could be continued, if desired, by additional chromatographic operations (ion exchange and/or gel permeation as described in the abovementioned French Patent Applications) so as to increase further the specific activity.

EXAMPLE 7

Production and purification of L-malyl-L-tyrosine ethyl ester in the presence of polyethylene glycol of average molar mass 600 as co-solvent (1) Synthesis 40.2 g of L-malic acid are dissolved in 50 g of 10 N aqueous sodium hydroxide solution, and the pH is then adjusted to 6.4 using 5 N aqueous sodium hydroxide solution so as to convert the L-malic acid into sodium L-malate. The solution obtained is diluted to 150 g with demineralized water (solution A).

110.2 g of L-tyrosine ethyl ester, in the form of the hydrochloride, are dissolved in 100 g of 1 N aqueous sodium hydroxide solution, the pH is adjusted to 6.4 with 1 N aqueous sodium hydroxide solution and the mixture is then diluted to 250 g with demineralized water (solution B).

The solutions A and B prepared above are mixed, the pH is checked and adjusted, if necessary, to a value of 6.4, and the mixture is then diluted to 450 g with demineralized water (solution C).

825 g of polyethylene glycol of average molar mass 600 (abbreviated to PEG 600) are added to the solution C, the mixture is agitated until a clear and homogeneous solution is obtained and this solution is then preheated to 40° C. The reaction is started by adding 225 g of the enzyme solution assaying at 55 U/ml (enzyme solution in 20 mM potassium phosphate buffer, pH 6.4, containing 0.1 mM manganese sulphate). The molar concentrations of the various ingredients in the reaction mixture (total volume 1.5 liters) are as follows: sodium L-malate: 200 mM; L-tyrosine ethyl ester: 300 mM; polyethylene glycol 600 : 55% (weight/volume); enzyme concentration: 8 U/ml.

After gentle agitation of the reaction medium for 24 hours at 40° C., the concentration of L-malyl-L-tyrosine ethyl ester in the reaction medium is 140 mM (yield: 70%), which corresponds to the presence of 210 millimoles of the ester in the reaction medium of volume 1.5 liters. The pH of the medium is then adjusted to between 3 and 4 with acidified water in order to inactivate the enzyme and so as to be able to extract the desired product from an organic phase, as described below. The total volume of the resulting aqueous solution is then 2.25 liters.

(2) Purification

The abovementioned aqueous solution is extracted with 3 volumes of ethyl acetate per volume of aqueous solution, and this extraction is repeated three times, the organic phase being separated from the aqueous phase on each occasion. 6.75 liters of ethyl acetate are hence used for 2.25 liters of aqueous solution at each extraction, equivalent to 21.25 liters of ethyl acetate in total. The ethyl acetate extracts are combined and concentrated by removal of the solvent under reduced pressure. 63 g of concentrated aqueous solution are recovered (extraction yield, 93%).

The concentrated aqueous solution of L-malyl-L-tyrosine ethyl ester obtained is diluted with acidified water to a volume of 1.5 liters. The resulting acidified aqueous solution still contains, apart from the desired product, a small amount of residual malic acid and a large amount of co-solvent (PEG 600). The purity of the product is approximately 50%. On the other hand, all the residual L-tyrosine ethyl ester has remained in the separated aqueous phase, and can be reused for a fresh synthesis.

A second series of extractions is then performed on the acidified aqueous solution containing the L-malyl-L-tyrosine ethyl ester with ethyl acetate, using 4 volumes of ethyl acetate/volume of acidified aqueous solution. After one extraction, the extraction yield is equal to 95% and the purity of the product is greater than 90%. After concentration by removal of the ethyl acetate under reduced pressure, the concentrated product obtained is diluted with water to a volume of 2 liters. This solution contains 60 g of L-malyl-L-tyrosine ethyl ester. The overall yield of the extractions is 88%.

The de-esterification of the product can then be performed by a procedure similar to that described in Example 1, to obtain L-malyl-L-tyrosine in the form of its disodium salt.

EXAMPLE 8

Synthesis of L-malyl-L-tyrosine ethyl ester in the presence of various cosolvents The general procedure of Example 7 is followed, except that the molar concentrations of the various ingredients in the reaction mixture are as follows:
Sodium L-malate: 100 mM
L-tyrosine ethyl ester: 250 mM
Enzyme concentration: 15 U/ml
Composition and proportion of the cosolvent: see table below.

The table below shows, in addition, the molar concentrations of L-malyl-L-tyrosine ethyl ester obtained and, in some cases, the reaction yields in %.

| Cosolvent, % (w/v) | L-Malyl-L-tyrosine ethyl ester, mM | Yield % |
|---|---|---|
| ethylene glycol 40% | 27 | 27 |
| triethylene glycol 50% | 48 | 48 |
| polyethylene glycol 200 (PEG 200) 50% | 47 | 47 |
| N,N-dimethyl-acetamide (DMA) 50% | 60 | 60 |
| 1,3-dimethyl-2-imidazolidinone (DMI) 50% | 50 | 50 |
| Sulfolane, 50% | 51 | 51 |
| Monoglyme (n = 1) 50% | 58 | 58 |
| glyme (n = 2) 50% | 60 | 60 |
| glyme (n = 3-8) 50% | 56 | 56 |
| glyme (n = 11) 50% | 56 | 56 |
| glyme (n = 22) 50% | 50 | 50 |
| glyme (n = 44) 50% | 51 | 51 |
| PEG 600 | | |
| 55% | 86 | |
| 65% | 63 | |
| PEG 1500 | | |
| 40% | 56 | |
| 55% | 77 | |
| 65% | 53 | |
| PEG 4000 | | |
| 40% | 54 | |
| 55% | 72 | |
| 65% | 45 | |
| PEG 20000 | | |
| 40% | 52 | |
| 50% | 67 | |
| PEG 35000 55% | 40 | |

EXAMPLE 9

Synthesis of L-malyl-L-tyrosine ethyl ester in the presence of Micrococcus caseolyticus cells The general procedure of Example 7 is followed, except that the molar concentrations of the various ingredients in the reaction mixture are as follows:
Sodium L-malate: 100 mM
L-tyrosine ethyl ester: 250 mM Reaction time: 3 h 30 min Enzyme: the concentration of cells used in the reaction medium is such that the enzyme activity, as measured under the standard conditions after rupture of the cells, is of the order of 17 U/ml. It should be noted, however, that the cells used in the reaction are not ruptured.

cosolvent: concentration and nature as shown in the table below, which also shows the results obtained.

| Cosolvent, % w/v | L-Malyl-L-tyrosine ethyl ester, mM | Yield, % |
|---|---|---|
| none | 8 | 8 |
| PEG 600 50% | 23 | 23 |
| triglyme (compound of formula II where n = 3), 50% | 45 | 45 |

It is self-evident that the embodiments described are only examples, and that they could be modified, in particular by the substitution of equivalent techniques, without thereby departing from the scope of the invention.

We claim:

1. L-tyrosine derivatives, characterized in that they have the general formula

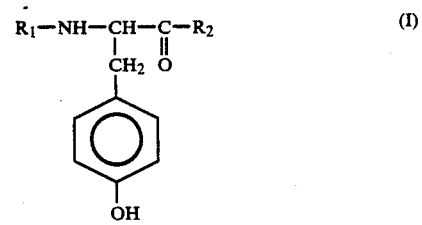

where $R_1$ is an L-malyl group, and $R_2$ is an —OH, —OM, methoxy, ethoxy or amino group, M denoting an alkali metal.

2. Compounds according to claim 1, characterized in that $R_2$ is an —OH or —OM group, M being an alakli metal.

* * * * *